United States Patent [19]

Detwiler et al.

[11] Patent Number: 5,429,931
[45] Date of Patent: Jul. 4, 1995

[54] MULTILAYER ANALYTICAL ELEMENT CONTAINING CROSSLINKED BINDER AND METHOD FOR THE DETERMINATION OF ETHANOL

[75] Inventors: Richard L. Detwiler, Webster; Stephen C. Hasselberg, Rochester; Ignazio S. Ponticello, Pittsford, all of N.Y.

[73] Assignee: Eastman Kodak Company, Rochester, N.Y.

[21] Appl. No.: 66,291

[22] Filed: May 24, 1993

[51] Int. Cl.[6] .................. C12Q 1/32; G01N 33/00
[52] U.S. Cl. .................................. 435/26; 435/4; 435/182; 436/106; 436/132; 422/57; 422/60
[58] Field of Search ............ 435/26, 4, 25, 182, 435/190; 436/106, 111, 128, 132; 422/56, 57, 60

[56] References Cited

U.S. PATENT DOCUMENTS

| | | | |
|---|---|---|---|
| 3,926,736 | 12/1975 | Bucolo | 435/26 |
| 4,481,292 | 11/1984 | Raymond | 435/147 |
| 4,788,153 | 11/1988 | Detwiler et al. | 436/97 |
| 4,810,633 | 3/1989 | Bauer et al. | 435/25 |
| 4,889,797 | 12/1989 | Amano et al. | 435/4 |
| 4,948,480 | 8/1990 | Christy et al. | 204/182.8 |
| 5,073,603 | 12/1991 | Ponticello | 525/350 |
| 5,086,143 | 2/1992 | Sutton et al. | 526/320 |
| 5,112,741 | 5/1992 | Palmer et al. | 435/25 |
| 5,141,854 | 8/1992 | Kaufman et al. | 435/26 |

FOREIGN PATENT DOCUMENTS 0464942 1/1992 European Pat. Off. .

OTHER PUBLICATIONS

Sigma Catalog 1993 *Diagnostic Reagents,* under the heading of Alcohol (Ethanol).

*Primary Examiner*—Michael G. Wityshyn
*Assistant Examiner*—Abdel A. Mohamed

[57] ABSTRACT

A multilayer analytical element has been prepared for accurate and rapid colorimetric determination of ethanol in aqueous specimens using alcohol dehydrogenase and an oxidized nicotinamide coenzyme. The element includes at least one reagent layer beneath a porous spreading layer. This reagent layer has a crosslinked polymeric binder prepared, in part, with a polymerizable monomer having a halomethylcarbonyl, haloethylcarbonyl, halomethylsulfonyl or haloethylsulfonyl group. Alcohol dehydrogenase is in a layer of the element for reaction with the analyte.

19 Claims, 4 Drawing Sheets

MULTILAYER ANALYTICAL ELEMENT CONTAINING CROSSLINKED BINDER AND METHOD FOR THE DETERMINATION OF ETHANOL

FIELD OF THE INVENTION

This invention relates to clinical chemistry. In particular, it relates to a multilayer analytical element and method for the quantitative determination of ethanol.

BACKGROUND OF THE INVENTION

Ethanol is a commonly encountered toxic substance. Methods for qualitative and quantitative determination of ethanol in body fluids, particularly human body fluids, are used in medicine and in law enforcement. In medicine, the level of ethanol in the blood is significant in diagnosing liver malfunction and alcoholism, as well as for understanding the reason for an emergency room patient being comatose. In law enforcement, such assays are used to determine whether or not an automobile operator is driving under the influence of alcohol.

Ethanol testing can be accomplished using both enzymatic and nonenzymatic assays. The nonenzymatic assays have a number of disadvantages and are being widely replaced by enzymatic assays which are more accurate, highly specific, more sensitive and require less expensive procedures. Enzymatic assays are generally based on the use of alcohol dehydrogenase to catalyze the reaction of ethanol to acetaldehyde. This reaction can be used alone, or in combination with other reactions to produce a spectrophotometric signal which can be related to the amount of ethanol in the tested specimen.

One enzymatic assay is based on the direct measurement of the reduced coenzyme (NADH), such as that described in U.S. Pat. No. 3,926,736 (Bucolo). This assay is carried out entirely in solution.

Another enzymatic assay is described in EP-A-0464 942 (published Jan. 1, 1992) which uses nicotinamide adenine dinucleotide (NAD+) as a coenzyme with alcohol dehydrogenase to produce the reduced form of the coenzyme. The coenzyme, in turn, reacts with a tetrazolium salt to produce a detectable dye. The described assay is carried out in a multilayer analytical element containing tris(hydroxymethyl)aminomethane buffer and both crosslinked and uncrosslinked gelatin layers.

One problem that has been encountered in developing a dry analytical element for the assay of ethanol is the strong interference by fluoride ion present in human serum. Fluoride ion is commonly used as a preservative in serum, and interferes in assays possibly by altering the equilibrium between ethanol and acetaldehyde, and causes the assay results to be biased positively compared to the true value of ethanol in the specimen. This problem has been effectively solved using a multilayer analytical element containing a high amount of buffer which is arranged in certain layers. Moreover, this element typically contains crosslinked gelatin as a binder for one or more of the reagent layers. Further details of such elements are found in U.S. application Ser. No. 08/005,683 (filed Jan. 19, 1993 by Detwiler) which is entitled MULTILAYER ANALYTICAL ELEMENT CONTAINING PRIMARY AMINE BUFFER AND METHOD FOR THE DETERMINATION OF ETHANOL.

While the element just described can be used effectively to detect ethanol, coating its many layers requires multiple steps and causes manufacturing inefficiencies. It would be desirable to reduce the number of coating steps in preparing an element which is just as effective in the detection of ethanol, and thus provide manufacturing efficiencies needed in the highly competitive field of clinical chemistry.

SUMMARY OF THE INVENTION

A highly effective analytical element useful for the determination of ethanol has been prepared with improved manufacturing efficiency. This element comprises a support having thereon, in order and in fluid contact:

a) a first reagent layer containing a buffer having a primary amine, the buffer maintaining the pH at from about 8 to about 10 during an assay for ethanol, and a binder comprising a crosslinked polymer derived by addition polymerization of:
   i) one or more ethylenically unsaturated monomers selected from the group consisting of an acrylamide and a vinyl pyrrolidone, and
   ii) an ethylenically unsaturated crosslinkable polymerizable monomer having a halomethylcarbonyl, haloethylcarbonyl, halomethylsulfonyl or haloethylsulfonyl group, the polymer having been crosslinked with a diamine or dithiol, and b) a porous spreading layer, the element further comprising alcohol dehydrogenase and an oxidized nicotinamide coenzyme.

This invention also provides a method for the detection of ethanol comprising:

A) contacting an aqueous fluid suspected of containing ethanol with the analytical element described above, and B) detecting the absorbence of the reduced form of the nicotinamide coenzyme as an indication of the presence of ethanol in the aqueous fluid.

The present invention provides a dry analytical element for the effective and specific detection of ethanol in a relatively short time using a signal generated by the reduction of a nicotinamide coenzyme by alcohol dehydrogenase. Manufacturing efficiencies in the reduction in the number of layers and required coating steps have been achieved.

These advantages have been achieved by having a particular crosslinked addition polymer as the binder in the bottom reagent layer of the element. At least one reagent layer previously used in the elements has been eliminated. The crosslinked addition polymer is prepared from either or both of an acrylamide and a vinyl pyrrolidone, and a crosslinkable monomer having halomethylcarbonyl, haloethylcarbonyl, halomethylsulfonyl or haloethylsulfonyl groups. Crosslinking is achieved using a diamine or dithiol which does not adversely affect the buffers or other reagents used in the element for ethanol detection. Particularly, the crosslinking agent is compatible with buffers containing primary amine groups.

DETAILED DESCRIPTION OF THE INVENTION

Figure 1:
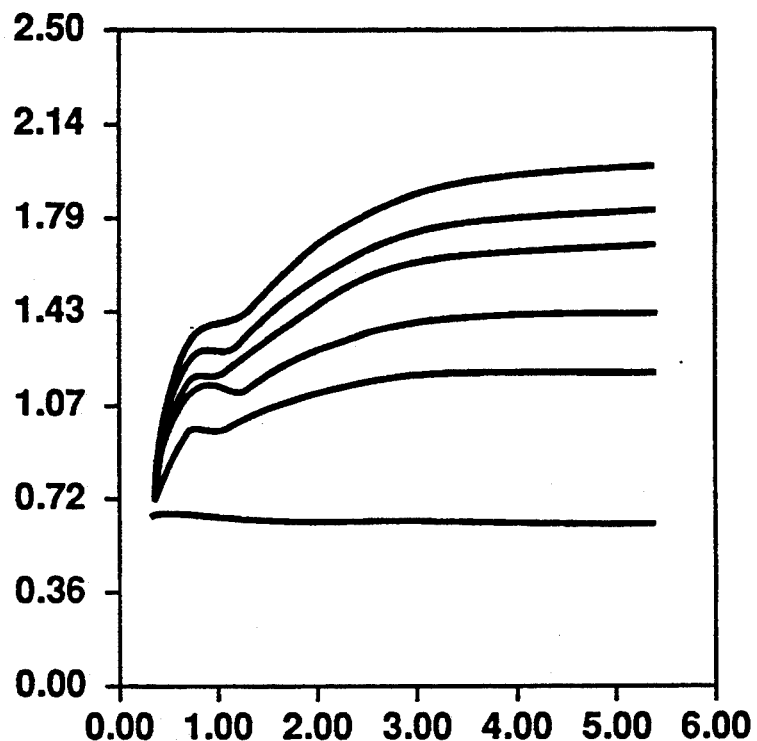
FIG. 1 is a graphical plot of data obtained in an assay for ethanol according to the present invention as described in Example 2 below with reflectance density ($D_R$) vs. time (minutes).

The element of this invention can be used to determine (that is, detect either the presence, amount or both) ethanol in biological fluids of animals or humans, but preferably in humans. Such fluids include, but are not limited to, whole blood, plasma, sera, lymph, bile, urine, semen, cerebral spinal fluid, spinal fluid, sputum, perspiration, synovial fluid, lacrimal fluid and stool specimens as well as other biological fluids readily apparent to one skilled in the art. Fluid preparations of tissues can also be assayed. Preferably, human serum is assayed with this invention.

In its broadest embodiment, the dry element of this invention has an inert support with two reagent layers and a porous spreading layer disposed thereon. The support is generally dimensionally stable, inert to chemical reaction and preferably transparent (that is, radiation transmissive for wavelengths between about 200 and 900 nm). However, non-transparent supports can be used if the mode of detection is reflectance spectroscopy instead of transmission spectroscopy. Useful supports are well known in the art, and include but are not limited to polyesters, papers, metal foils and polystyrene, polycarbonates and cellulose esters.

The porous spreading zone is prepared from any of the known materials used for such zones as described, for example in U.S. Pat. No. 4,292,272 (Kitajima et al), U.S. Pat. No. 3,992,158 (Przybylowicz et al), U.S. Pat. No. 4,258,001 (Pierce et al) U.S. Pat. No. 4,430,436 (Koyama et al), and JP 57(1982)-101760 (published Jun. 24, 1982). It is desired that the spreading zone be isotropically porous, meaning that the porosity is the same in each direction in the zone as caused by interconnected spaces or pores between particles, fibers or polymeric strands.

Preferred spreading zones are those described in U.S. Pat. No. 3,992,158 as "blush polymer" zones. Such zones can be formed on a supporting material by dissolving a polymer in a mixture of two organic liquids, one of which is a lower boiling, good solvent for the polymer and other being a high boiling, non-solvent or poor solvent for the polymer. The resulting polymer formulation is coated on the supporting material and dried under controlled conditions to leave an isotropically porous zone. Various polymers are known to be useful in this context including, but not limited to, polycarbonates, polyamides, polyurethanes and cellulose esters such as cellulose acetate (which is preferred).

Within the porous zone can be incorporated particulate materials of various sizes to enhance the void volume. Useful particulate materials include, but are not limited to, inorganic pigments such as titanium dioxide, barium sulfate, zinc oxide and lead oxide, with barium sulfate and titanium dioxide being preferred. Further details of the preparation of "blush polymers" are described in U.S. Pat. No. 3,992,158 (noted above).

The elements have at least one other layer which can contain one or more reagents needed for the assay. All of the layers are generally in fluid contact with each other, meaning that fluids, reagents and reagent products can pass or be transported between superposed regions of adjacent layers, unless of course, a reagent is immobilized in some manner so it will not migrate within or without a layer.

A first reagent layer which is adjacent the support is composed of one or more crosslinked polymers as binders. The crosslinked polymer is prepared by conventional addition polymerization of at least two (preferably three) types of ethylenically unsaturated polymerizable monomers.

One type of monomer is an acrylamide (or mixture thereof) or a vinyl pyrrolidone. Acrylamides include, but are not limited to, acrylamide, N-isopropylacrylamide, N-(1,1-dimethyl-3-oxobutyl)acrylamide, 2-acrylamido-2-hydroxymethyl-1,3-propanediol, N-(3-dimethylaminopropyl)acrylamide, N,N-dimethylacrylamide, N,N-diethylacrylamide, 3-(2-dimethylaminoethyl)acrylamide, and others readily apparent to one skilled in the art. The corresponding methacrylamides are also included. Acrylamide is preferred.

Vinyl pyrrolidones (or mixture thereof) include, but are not limited to, N-vinyl-2-pyrrolidone and others readily apparent to one skilled in the art. N-vinyl-2-pyrrolidone is preferred.

The first type of monomer (that is, acrylamide or vinyl pyrrolidone) is used in an amount of from about 90 to about 99.8 weight percent, and preferably at from about 96.5 to about 99 weight percent.

Preferably, both an acrylamide and a vinyl pyrrolidone are copolymerized to prepare the crosslinkable polymer. In such embodiments, preferably from about 40 to about 60 weight percent of an acrylamide, and from about 40 to about 60 weight percent of a vinyl pyrrolidone are used.

The second type of monomer used is a crosslinkable monomer having a halomethylcarbonyl, haloethylcarbonyl, halomethylsulfonyl or haloethylsulfonyl group which is crosslinkable with a diamine or dithiol. Useful monomers having halomethylcarbonyl or haloethylcarbonyl groups, which are preferred, include, but are not limited to, vinyl chloroacetate, N-(3-chloroacetamidopropyl)methacrylamide, 2-chloroacetamidoethyl methacrylate, 4-chloroacetamidostyrene, 2-chloroacetamidocarbonyliminoethyl methacrylate, m- & p-chloroacetamidomethylstyrene, N-(3-chloroacetamidocarbonyliminopropyl)methacrylamide, 4-chloroacetamidocarbonyliminostyrene, m- & p-chloroacetamidocarbonyliminomethylstyrene, N-vinyl-N'-(3-chloropropionyl)urea, 4-(3-chloropropionamido)styrene, 4-(3-chloropropionamidocarbonylimino)styrene, 2-(3-chloropropionamido)ethyl methacrylate and N-[2-(3-chloropropionamido)ethyl]-methacrylamide. A most preferred monomer is N-(3-chloroacetamidopropyl)methacrylamide.

Monomers having crosslinkable halomethylsulfonyl or haloethylsulfonyl groups include, but are not limited to, p-(2-chloroethylsulfonylmethyl)styrene, N-(4-chloroethylsulfonylmethylphenyl) acrylamide, N- [3-(2-chloroethylsulfonyl)propionamidomethyl]acrylamide, 2-{3-[2-(2-chloroethylsulfonyl)ethyl]propionyloxy}ethyl acrylate and others described in U.S. Pat. No. 4,161,407. (Campbell) and U.S. Pat. No. 4,548,870 (Ogawa et al).

The amount of the second type of monomer is generally from about 0.2 to about 10, and preferably from about 1 to about 3.5, weight percent.

It is well known that the haloethylsulfonyl and haloethylcarbonyl groups of polymers derived from monomers containing such groups can be readily dehydrohalogenated to vinylsulfonyl and vinylcarbonyl groups which are also readily crosslinkable with amine and sulfhydryl groups containing crosslinking agents in accordance with this invention, and such derived polymers are also within the scope of useful polymers of the present invention.

Useful crosslinking agents are compounds having two or more amino of sulfhydryl (or mercapto) groups, and include, but are not limited to, ethylenediamine, 1,3-propanediamine, 1,3-propanedithiol, dithiothreitol, dithioerythritol and butylenediamine. The amount of crosslinking agent is generally from about 0.25 to about 1.5 equivalents, and preferably from about 0.5 to about 1.1 equivalents, per mole of hardening site in the polymer. Crosslinking is generally carried out during and immediately after the coating and drying operation.

The polymers described herein can be prepared using conventional addition polymerization techniques using redox initiator systems or organic soluble free radical generating initiating systems. The polymers are preferably prepared in solution using a redox initiator system and a mixture of water and isopropanol as the solvent.

Useful crosslinkable polymers include, but are not limited to, poly[acrylamide-co-N-vinyl-2-pyrrolidone-co-N-(3-chloroacetamidopropyl)methacrylamide], poly[acrylamide-co-N-vinyl-2-pyrrolidone-co-p-(2-chloroethylsulfonylmethyl)styrene], poly{acrylamide-co-N-vinyl-2-pyrrolidone-co-N-[4-(2-chloroethylsulfonylmethyl)phenyl]acrylamide}, poly[N-vinyl-2-pyrrolidone-co-N-(3-chloroacetamidopropyl)methacrylamide], poly[acrylamide-co-N-(3-chloroacetamidopropyl)methacrylamide], poly(acrylamide-co-N-vinyl-2-pyrrolidone-co-4-chloroacetamidostyrene), poly[acrylamide-co-N-vinyl-2-pyrrolidone-co-4-(3-chloropropionamido)styrene] and poly(acrylamide-co-N-vinyl-2-pyrrolidone-co-4-chloroacetamidocarbonyliminostyrene).

The amount of crosslinked polymer in the first reagent layer will depend upon the amount of reagent to be dispersed, but is generally at least about 5 g/m$^2$, with from about 6 to about 15 g/m$^2$ being preferred.

When the element contains a second reagent layer, the same or different (or mixtures thereof) binders can be used therein. Alternative binders include gelatin (hardened or unhardened), poly(vinyl alcohol), acrylamide polymers, vinylpyrrolidone polymers or copolymers of acrylamide and a vinylpyrrolidone monomer. Gelatin is preferred in the second reagent layer.

The buffer used in the element (in one or more layers) is one which has a primary amine and maintains the pH of the layers during an assay at from about 8 to about 10, and preferably at from about 8.5 to about 9. A number of such buffers are known and commercially available. They include, but are not limited to, tris(hydroxymethyl)aminomethane, tris(methyl)aminomethane, and their acid forms (addition salts of HCl, HF and the like), and tris(hydroxymethyl)aminomethane glutamate. Tris(hydroxymethyl)aminomethane or tris(hydroxymethyl)aminomethane hydrofluoride is preferred. The same or different buffers can be used in the layers of the element.

The amount of buffer in each reagent layer is generally at least about 25 mmoles/m$^2$, and from about 30 to about 50 mmoles/m$^2$ is preferred. It is not necessary, but it is preferred, that the amounts in multiple reagent layers be the same. For the preferred buffers, the preferred amount in each layer is about 41 mmoles/m$^2$ which corresponds to about 5 g/m$^2$.

The element also contains alcohol dehydrogenase which can be obtained from a number of commercial sources. Generally, the enzyme is present in one or more reagent layers in an amount of from about 5000 to about 30,000 I.U./m$^2$. As used in this application, one I.U. represents the International Unit for enzyme activity and is defined as the amount of enzyme activity required to catalyze the conversion of 1 micromole of substrate per minute under standard pH and temperature conditions. For alcohol dehydrogenase, the standard conditions are 25° C. and a pH of about 8. Preferably, the alcohol dehydrogenase is present in the second reagent layer where the element contains two or more reagent layers.

Within one or more layers of the element is an oxidized nicotinamide coenzyme which can be reduced to provide a detectable colorimetric signal upon reaction with ethanol as catalyzed by alcohol dehydrogenase. Useful oxidized coenzymes include, but are not limited to, oxidized nicotinamide adenine dinucleotide (NAD+) and oxidized nicotinamide adenine dinucleotide phosphate (NADP+). For example, in the assay, NADH absorbs at about 340 nm, and NAD+ absorbs at about 260 nm. Preferably, the coenzyme is in the porous spreading layer.

Optionally, but preferably, the porous spreading layer is separated from the reagent layers with a hydrophilic subbing layer composed of one or more suitable hydrophilic binder materials. Such materials include, but are not limited to gelatin and other colloidal materials, polymers of vinyl pyrrolidone, vinyl alcohol, acylamide, N-alkylsubstituted acrylamide (such as N-isopropylacrylamide), including copolymers thereof, and other materials readily apparent to one skilled in the art.

One or more layers of the element can also contain one or more useful materials, such as antioxidants, coating aids, surfactants, bacteriostats and other materials known in the art to facilitate coating of the layers, reagent stability and fluid spreading during the assay.

A variety of different elements, depending upon the method and equipment for assay, can be prepared in accordance with this invention. They can be configured in a variety of forms and shapes, including elongated tapes of any desired width, sheets, slides or chips. Preferred elements are configured as test slides like those commercially available under the EKTACHEM ™ trademark for a variety of clinical assays. Such test slides are described in a considerable number of patents and other publications. Generally, the layers are formed on a suitable support by applying specific aqueous or solvent-based formulations of individual layer compositions in sequence using suitable coating equipment, and procedures followed by drying.

In a preferred embodiment, a multilayer analytical element of this invention comprises a nonporous, transparent support having thereon, in order and in fluid contact:
- a first reagent layer containing a buffer having a primary amine as defined above mixed with the crosslinked binder described herein,
- a second reagent layer comprising alcohol dehydrogenase and the same buffer as described for the first reagent layer mixed in a hydrophilic binder,
- a hydrophilic subbing layer, and
- a porous spreading layer containing an oxidized nicotinamide coenzyme.

The assay of this invention can be manual or automated. In general, the element is used by physically contacting it with the test specimen (for example, from 1 to 200 μl) suspected of containing ethanol under ambient conditions (although other temperatures can be used). The specimen and reagents become mixed within the layers of the element and any ethanol present in the specimen reacts with the oxidized nicotinamide coenzyme to produce the reduced form which is detectable as described above. Contact can be achieved in any suitable manner, for example by dipping or immersing the element into the specimen or preferably, by spotting the specimen onto the element by hand, machine or suitable dispensing means.

After specimen application, the element is exposed to any conditioning, such as incubation, heating or otherwise, that may be desirable to quicken or otherwise facilitate obtaining a test result.

Generally within about 5 minutes, a spectrophotometric measurement is made. This measurement can be made using suitable reflection or transmission spectrophotometric equipment and procedures as a measure of ethanol concentration in the test sample. Generally, the detectable signal is measured at a wavelength in the range of from about 320 to about 360 nm.

The following examples are included to illustrate the practice of this invention, and are not meant to be limiting in any way. The materials used in the examples were obtained as follows:

ESTANE TM 5715 polyurethane resin from B. F. Goodrich, TRITON TM X-100 nonionic surfactant and TRITON TM X-200E anionic surfactant from Rohm and Haas (rights now owned by Union Carbide), and the remainder of the materials from Eastman Kodak Company or other commercial sources, or they were prepared using standard procedures and readily available starting materials.

EXAMPLE 1 Preferred Analytical Element for Ethanol Determination

The preferred element of this invention and amounts of components are illustrated in the structure:

|  |  | Dry Coverage (g/m$^2$) |
|---|---|---|
| Spreading Layer | Barium sulfate | 105 |
|  | Cellulose acetate | 8 |
|  | ESTANE TM 5715 polyurethane | 1.1 |
|  | TRITON TM X-405 nonionic surfactant | 2.1 |
|  | NAD+ | 8 |
| Subbing Layer | Poly(N-isopropylacrylamide) | 0.4 |
|  | Gelatin (unhardened) | 6 |
| Second Reagent Layer | Tris(hydroxymethyl)-aminomethane (pH 8.75) | 5 |
|  | Ottasept | 0.02 |
|  | TRITON TM X-200E anionic surfactant | 0.01 |
|  | TRITON TM X-100 nonionic surfactant | 0.02 |
|  | Alcohol dehydrogenase | 10,000* |
|  | Bovine serum albumin | 1.75 |
| First Reagent Layer | Crosslinked polymer** | 8.78 |
|  | SURFACTANT 10G nonionic surfactant | 0.13 |
|  | TRITON TM X-200E anionic surfactant | 0.002 |
|  | Ottasept | 0.02 |
|  | Tris(hydroxymethyl)aminomethane (pH 8.75) | 5 |
|  | Dithiothreitol | 0.16 |
|  | Poly(ethylene terephthalate) Support |  |

*I.U./m$^2$
**Poly[acrylamide-co-N-vinyl-2-pyrrolidone-co-N-(3-chloroacetamidopropyl)methacrylamide](48.75:48.75:2.5 weight ratio)

EXAMPLE 2 Determination of Ethanol

This example demonstrates the use of the element of this invention. Analytical elements were prepared having the format and components described in Example 1, and were mounted into slides for use in a conventional EKTACHEM TM clinical analyzer.

A second set of elements of this invention were similarly prepared having the same format and components, except that the second reagent layer contained poly(acrylamide-co-N-vinylpyrrolidone)(50:50 weight ratio) at a level of 8.78 g/m$^2$ in place of the gelatin, and the TRITON TM X-200E anionic surfactant was omitted.

A third set of elements (Controls) outside the scope of this invention were also prepared having the format and components noted below. It did not contain the crosslinkable polymer described in this application. Therefore, the elements required the presence of a third reagent layer separating the first and second reagent layers to prevent the hardener from reacting with the buffer rather than the gelatin. The Control elements had the structure:

|  |  | Dry Coverage (g/m$^2$) |
|---|---|---|
| Spreading Layer | Barium sulfate | 105 |
|  | Cellulose acetate | 8 |
|  | ESTANE TM 5715 polyurethane | 1.1 |
|  | TRITON TM X-405 nonionic surfactant | 2.1 |
|  | NAD+ | 8 |
| Subbing Layer | Poly(N-isopropylacrylamide) | 0.4 |
|  | Gelatin (unhardened) | 6 |
| Second Reagent Layer | Tris(hydroxymethyl)-aminomethane (pH 8.75) | 5 |
|  | Ottasept | 0.02 |
|  | TRITON TM X-200E anionic surfactant | 0.01 |
|  | TRITON TM X-100 nonionic surfactant | 0.02 |
|  | Alcohol dehydrogenase | 10,000* |
|  | Bovine serum albumin | 1.75 |
| Third Reagent Layer | Gelatin (pH 7.5) | 2 |
|  | TRITON TM X-100 nonionic surfactant | 0.02 |
|  | TRITON TM X-200E anionic surfactant | 0.013 |
|  | Bis(vinylsulfonylmethyl)-ether hardener | 0.16 |
| First Reagent Layer | Gelatin | 6 |
|  | TRITON TM X-100 nonionic surfactant | 0.02 |

-continued

|  |  | Dry Coverage (g/m²) |
|---|---|---|
|  | TRITON ™ X-200E anionic surfactant | 0.01 |
|  | Ottasept | 0.02 |
|  | Tris(hydroxymethyl)amino-methane (pH 8.75) | 5 |
|  | Poly(ethylene terephthalate) Support |  |

*I.U./m²

All of the elements were evaluated for ethanol determination by applying fluid samples containing a range of levels (0 to 500 mg/dl) of ethanol to individual elements, and plotting the resulting rate of color formation in reflectance density (y-axis) vs. time in minutes (x-axis) for the various ethanol levels. The results are shown in FIG. 1 for the elements of Example 1, in FIG. 2 for the elements of Example 2, and in FIG. 3 for the Control elements. The approximate amounts of ethanol in the fluid samples were 0, 50, 100, 200, 300 and 500 mg/dl.

Figure 2:
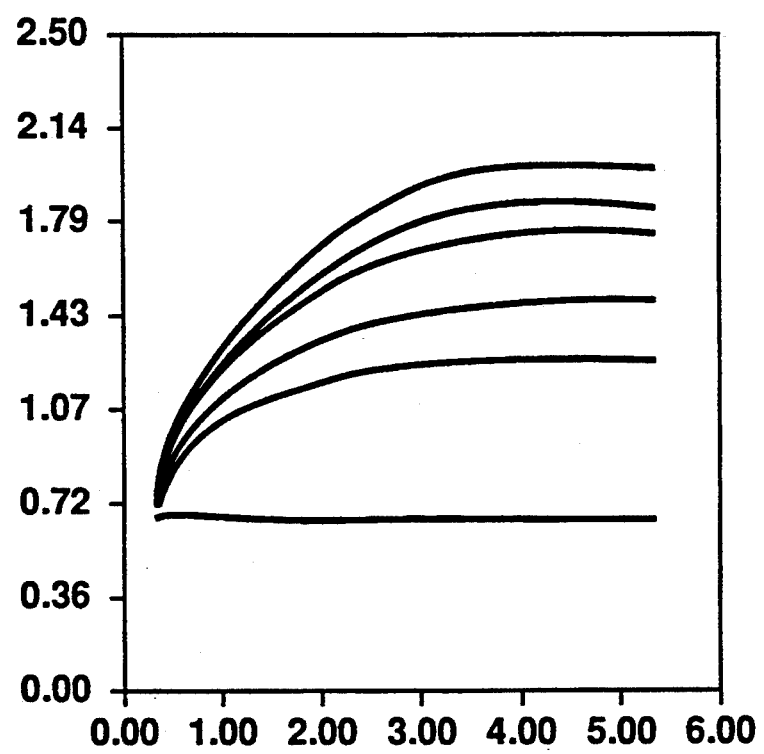
FIG. 2 is a graphical plot of data obtained in an assay for ethanol according to the present invention as de
Figure 3:
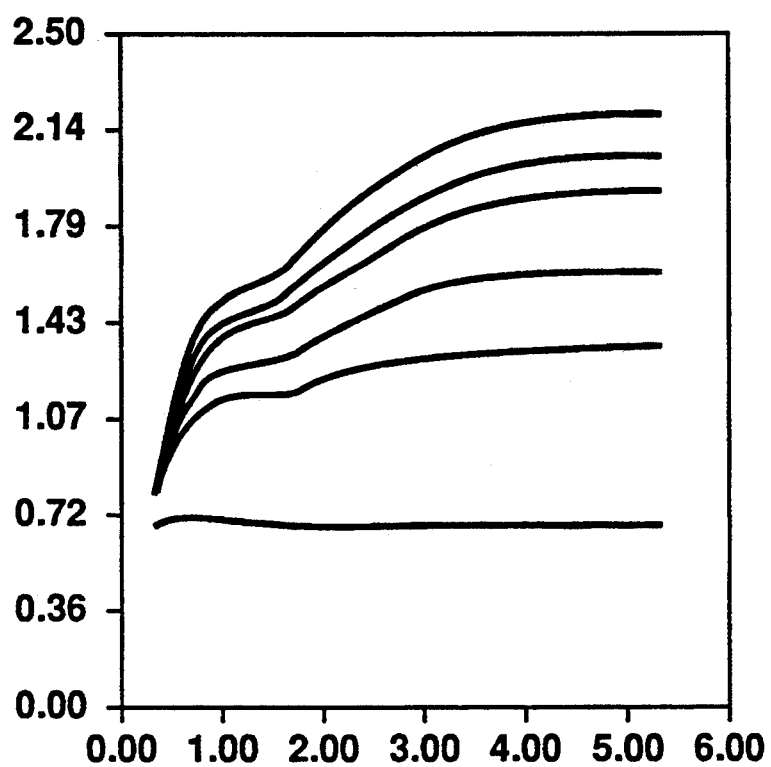
- FIG. 3 is a graphical plot of data obtained in an assay for ethanol of Control elements as described in Example 2 below with reflectance density ($D_R$) vs. time (minutes).

An improvement in sensitivity may be indicated by the leveling out of the plotted curves in FIGS. 1 and 2 for the elements of the invention before five minutes of reaction time. However, the plotted curves in FIG. 3 are shown to be increasing after five minutes of reaction time, indicating that the reaction in the assay is not complete at that time. It should be noted that the improvement in sensitivity was achieved while eliminating a reagent layer in the element, resulting in considerable savings in manufacturing.

EXAMPLES 3–4 Analytical Elements Containing Single Reagent Layer

These examples demonstrate the practice of this invention with analytical elements having a single reagent layer. Three variations of such elements were prepared having the formats and components described below. Control elements were similarly prepared having the format and components like the Control elements of Example 2 except that the amount of bis(vinylsulfonylmethyl) ether was only 0.14 g/m².

Figure 4:
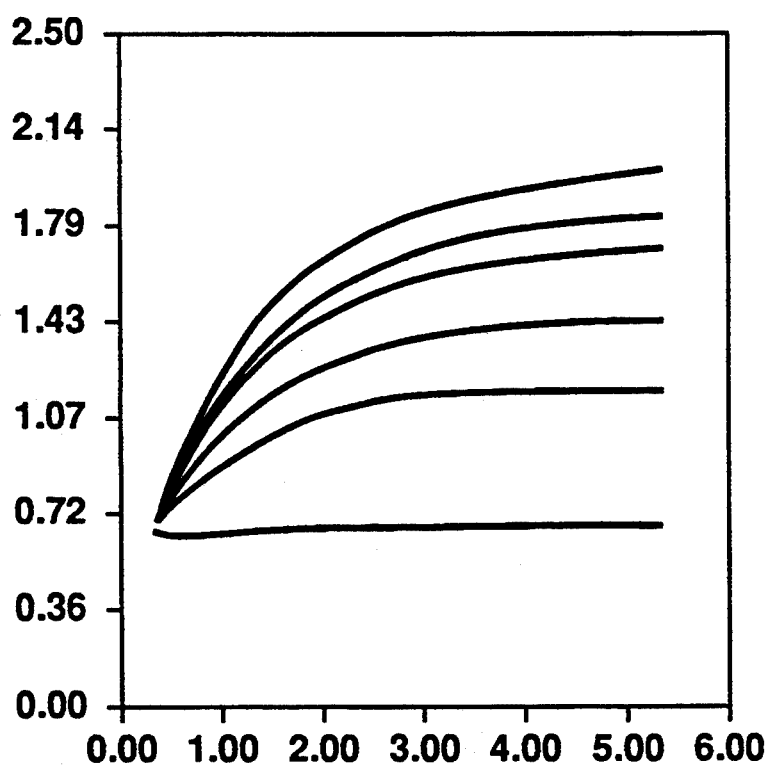
FIG. 4 is a graphical plot of data obtained in an assay for ethanol according to the present invention as described in Example 3 below with reflectance density ($D_R$) vs. time (minutes).
Figure 5:
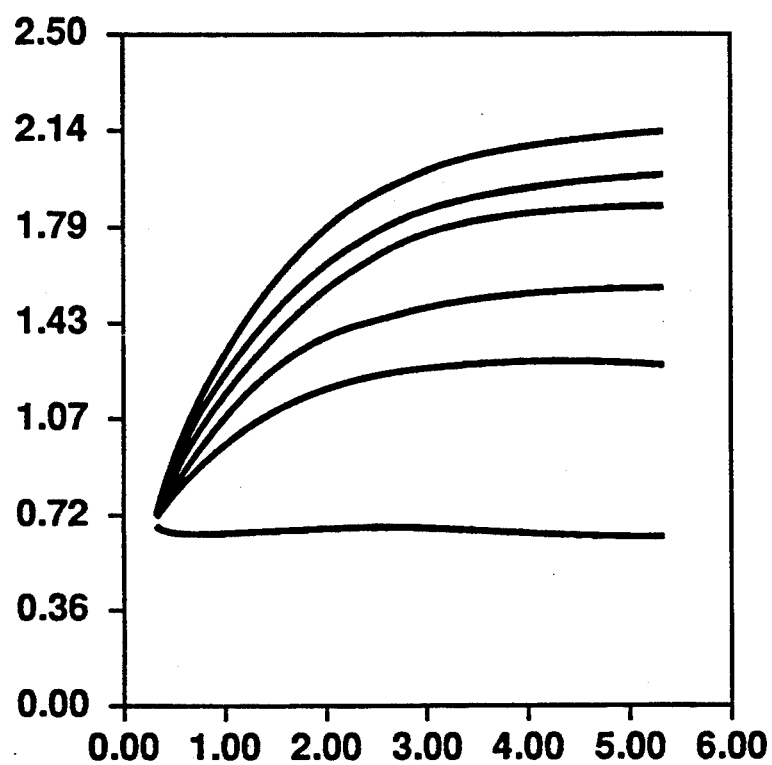
FIG. 5 is a graphical plot of data obtained in an assay for ethanol according to the present invention as described in Example 4 below with reflectance density ($D_R$) vs. time (minutes).
Figure 6:
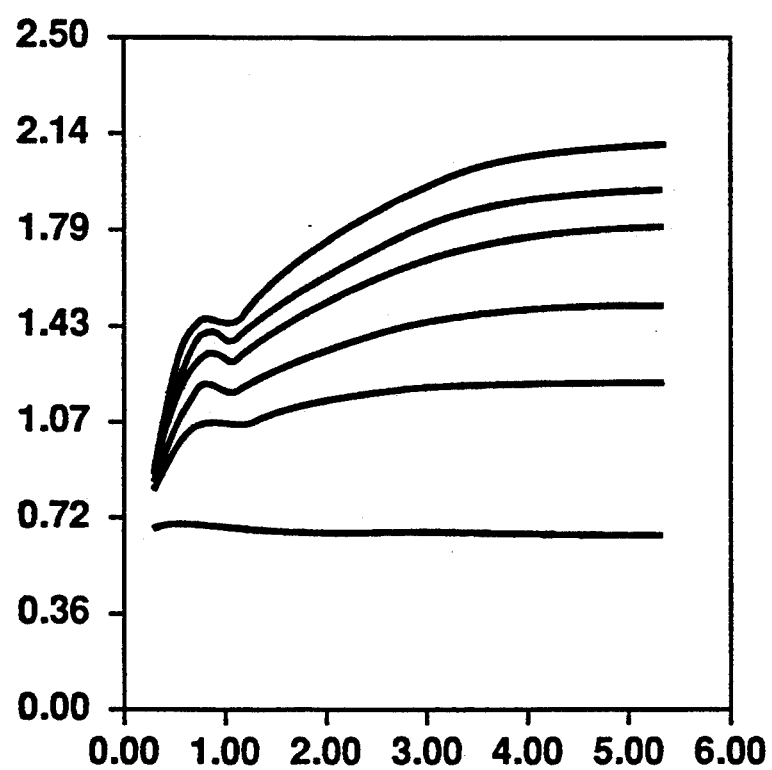
FIG. 6 is a graphical plot of data obtained in an assay for ethanol of Control elements as described in Examples 3–4 below with reflectance density ($D_R$) vs. time (minutes).

All of the elements were evaluated using the procedure described in Example 2, and the results are similarly shown in FIGS. 4, 5 and 6 (reflectance density on the y-axis and time in minutes on the x-axis). FIGS. 4 and 5 are for the elements of this invention (Examples 3 and 4, respectively), and FIG. 6 is for the Control elements.

The elements had the format and components as defined below.

|  |  | Dry Coverage (g/m²) |
|---|---|---|
| Spreading Layer | Barium sulfate | 105 |
|  | Cellulose acetate | 8 |
|  | ESTANE ™ 5715 polyurethane | 1.1 |
|  | TRITON ™ X-405 nonionic surfactant | 2.1 |
|  | NAD⁺ | 8 |
| Subbing Layer | Poly(N-isopropylacrylamide) | 0.4 |
| Reagent Layer | Tris(hydroxymethyl)-aminomethane (pH 8.75) | 5 |
|  | Ottasept | 0.02 |
|  | TRITON ™ X-200E anionic surfactant | 0.01 |
|  | TRITON ™ X-100 nonionic surfactant | 0.022 |
|  | Alcohol dehydrogenase | 10,000* |

-continued

|  |  | Dry Coverage (g/m²) |
|---|---|---|
|  | Bovine serum albumin | 1.75 |
|  | Crosslinked polymer** | 12 |
|  | Dithiothreitol | 0.16 |
|  | Poly(ethylene terephthalate) Support |  |

*I.U./m²
**Poly[acrylamide-co-N-vinyl-2-pyrrolidone-co-N-(3-chloroacetamidopropyl)methacrylamide](48.75:48.75:2.5 weight ratio) for Examples 3 and 4.

The element for Example 3 is as shown above, while the element for Example 4 contained 0.024 g/m² of TRITON™X-100 nonionic surfactant and 0.32 g/m² of dithiothreitol.

The invention has been described in detail with particular reference to preferred embodiments thereof, but it will be understood that variations and modifications can be effected within the spirit and scope of the invention. All patents, patent applications (published or unpublished, domestic or foreign), journal literature, books and other published prior art cited herein are incorporated herein by reference for the teaching therein pertinent to this invention to the extent allowed by U.S. statute and regulations.

We claim:

1. An analytical element for the determination of ethanol comprising a support having thereon, in order and in fluid contact:

a) a first reagent layer containing a buffer having a primary amine, said buffer maintaining the pH at from about 8 to about 10 during an assay for ethanol, and a binder comprising a crosslinked polymer derived by addition polymerization of:

i) one or more ethylenically unsaturated polymerizable first monomers selected from the group consisting of an acrylamide and a vinyl pyrrolidone, and ii) an ethylenically unsaturated crosslinkable polymerizable second monomer having a halomethylcarbonyl, haloethylcarbonyl, halomethylsulfonyl or haloethylsulfonyl group, said polymer having been crosslinked with a diamine or dithiol, and b) a porous spreading layer, said element further comprising an alcohol dehydrogenase and an oxidized nicotinamide coenzyme.

2. The element of claim 1 wherein said second monomer has a halomethylcarbonyl or haloethylcarbonyl group.

3. The element of claim 1 wherein said one or more first monomers are selected from the group consisting of vinyl chloroacetate, N-(3-chloroacetamidopropyl)-methacrylamide, 2-chloroacetamidoethyl methacrylate, 4chloroacetamidostyrene, p-chloracetamidomethylstyrene, N-(3-chloroacetamidocarbonyliminopropyl)methacrylamide, 2-chloroacetamidocarbonyliminoethyl methacrylate, 4-chloroacetamidocarbonyliminostyrene, m & p-chloroacetamidocarbonyliminomethylstyrene, N-vinyl-N'-(3-chloropropionyl)urea, 4-(3-chloropropionamido)styrene, 4-(3-chloropropionamidocarbonylimino)styrene, 2-(3-chloropropionamido) ethyl methacrylate and N-[2-(3-chloropropionamido)ethyl]-methacrylamide.

4. The element of claim 1 wherein said crosslinked polymer is derived from acrylamide, N-vinyl-2-pyrrolidone and N-(3-chloroacetamidopropyl)methacrylamide.

5. The element of claim 1 wherein said crosslinked polymer in prepared from about 90 to about 99.8 weight percent of said one or more first monomers, and from about 0.2 to about 10 weight percent of said second monomer.

6. The element of claim 1 wherein said buffer is tris(hydroxymethyl)aminomethane, tris(methyl)aminomethane or tris(hydroxymethyl)aminomethane glutamate.

7. The element of claim 6 wherein said buffer is tris(hydroxymethyl)aminomethane.

8. The element of claim 1 wherein said oxidized nicotinamide coenzyme is in said porous spreading layer which is formed from a blush polymer.

9. The element of claim 1 wherein said binder in said first reagent layer has been crosslinked with ethylenediamine, 1,3-propanediamine, 1,3-propanediol, dithiothreitol, dithioerythritol or butylenediamine.

10. The element of claim 1 further comprising a second reagent layer between said first reagent layer and said porous spreading layer, said second reagent layer containing an alcohol dehydrogenase in a hydrophilic binder.

11. The element of claim 10 wherein said second reagent layer comprises gelatin as said hydrophilic binder.

12. The element of claim 10 wherein said first and second reagent layers comprise the same binder.

13. The element of claim 1 wherein said nicotinamide coenzyme is nicotinamide adenine dinucleotide.

14. The element of claim 10 further comprising a subbing layer between said second reagent layer and said porous spreading layer.

15. A method for the detection of ethanol comprising:
A) contacting an aqueous fluid suspected of containing ethanol with an analytical element comprising a support having thereon, in order and in fluid contact:
a) a first reagent layer containing a buffer having a primary amine, said buffer maintaining the pH at from about 8 to about 10 during said method, and a binder comprising a crosslinked polymer derived by addition polymerization of:
i) one or more ethylenically unsaturated polymerizable monomers selected from the group consisting of acrylamide and a vinyl pyrrolidone, and
ii) an ethylenically unsaturated crosslinkable polymerizable monomer having a halomethylcarbonyl, haloethylcarbonyl, halomethylsulfonyl or haloethylsulfonyl group, said polymer having been crosslinked with a diamine or dithiol, and
b) a porous spreading layer,
said element further comprising alcohol dehydrogenase and an oxidized nicotinamide coenzyme, and
B) detecting the absorbence of the reduced form of said nicotinamide coenzyme as an indication of the presence of ethanol in said aqueous fluid.

16. The method of claim 15 wherein said detection step B) is carried out within about 5 minutes of said contacting step A).

17. The method of claim 15 wherein said aqueous fluid is human whole blood, serum or plasma.

18. The method of claim 15 wherein said ethanol is detected from measuring the absorbence of the reduced form of nicotinamide adenine dinucleotide.

19. The method of claim 15 wherein said buffer maintains the pH of said element at from about 8.5 to about 9.

* * * * *